(12) United States Patent
Bimczok et al.

(10) Patent No.: US 7,687,055 B2
(45) Date of Patent: Mar. 30, 2010

(54) METHOD OF TREATING KERATINIC FIBERS WITH CREATINE, CREATININE AND/OR THEIR SALTS TO STRENGTHEN, RESTRUCTURE, HARDEN AND STABILIZE THEM

(75) Inventors: Rudolf Bimczok, Seeheim-Jugenheim (DE); Thomas Kripp, Fraenkisch-Crumbach (DE); Beate Grasser, Hattersheim (DE); Christian Springob, Bensheim (DE)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 10/363,620

(22) PCT Filed: Mar. 14, 2002

(86) PCT No.: PCT/EP02/02839

§ 371 (c)(1), (2), (4) Date: Jul. 28, 2003

(87) PCT Pub. No.: WO02/076408

PCT Pub. Date: Oct. 3, 2002

(65) Prior Publication Data

US 2004/0018162 A1  Jan. 29, 2004

(30) Foreign Application Priority Data

Mar. 24, 2001 (DE) .................... 101 14 561

(51) Int. Cl.
*A61Q 5/00* (2006.01)
*A01N 37/44* (2006.01)

(52) U.S. Cl. .................. 424/70.1; 424/401; 514/551; 514/561; 514/564; 514/880

(58) Field of Classification Search ............... 424/401, 424/70.1; 514/551, 561, 564, 880
See application file for complete search history.

(56) References Cited

U.S. PATENT DOCUMENTS

| | | | | |
|---|---|---|---|---|
| 3,957,971 A | * | 5/1976 | Oleniacz | 424/450 |
| 4,551,330 A | * | 11/1985 | Wagman et al. | 424/59 |
| 4,975,275 A | * | 12/1990 | Mitamura et al. | 424/70.1 |
| 5,886,042 A | * | 3/1999 | Yu et al. | 514/557 |
| 6,242,491 B1 | * | 6/2001 | Kaddurah-Daouk | 514/565 |
| 6,432,424 B1 | * | 8/2002 | Shapiro et al. | 424/401 |
| 6,482,808 B1 | * | 11/2002 | Springob et al. | 514/99 |
| 2002/0044913 A1 | * | 4/2002 | Hamilton | 424/59 |

FOREIGN PATENT DOCUMENTS

| | | | |
|---|---|---|---|
| DE | 37 09 459 A | | 10/1987 |
| DE | 39 41 534 A | | 6/1990 |
| DE | 198 41 385 A | | 3/2000 |
| EP | 0 565 010 A | | 10/1993 |
| FR | 2 725 896 A | | 4/1996 |
| GB | 2357970 A | * | 7/2001 |
| JP | 6-240579 A | * | 8/1994 |
| WO | 00/57839 | | 10/2000 |
| WO | WO 00/57839 A1 | * | 10/2000 |
| WO | 01 00203 A | | 1/2001 |
| WO | 02 02075 A | | 1/2002 |

OTHER PUBLICATIONS

Patent Abstracts of Japan vol. 018, No. 632 (C-1280), Dec. 2, 1994 & JP 06 240579 A, Aug. 30, 1994.
Database Promt "Online! "Natural Ingredients" Retrieved From STN Databases Accession No. 2002: 414055 XP 002218034 Siehe "Cosmocair C100" & Household & Personal Products Industry, BD. 39, NR. 6, Jun. 6, 2002, Seite 76 (8).

* cited by examiner

*Primary Examiner*—Sreeni Padmanabhan
*Assistant Examiner*—Renee Claytor
(74) *Attorney, Agent, or Firm*—Michael J. Striker

(57) ABSTRACT

The method of hardening, fortifying, restructuring, repairing, increasing volume or stabilizing keratinic fibers, especially human hair, includes providing a keratinic fiber treatment composition containing from 0.05 to 1.0 percent by weight of creatine, a salt of creatine, creatinine and/or a salt of creatinine, bringing the keratinic fiber treatment composition into contact with the keratinic fibers and allowing the keratinic fiber treatment composition to remain in contact with the keratinic fibers for a certain time interval.

6 Claims, No Drawings

METHOD OF TREATING KERATINIC FIBERS WITH CREATINE, CREATININE AND/OR THEIR SALTS TO STRENGTHEN, RESTRUCTURE, HARDEN AND STABILIZE THEM

This is the U.S. National Stage of PCT Application No. PCT/EP 02/02839, filed on Mar. 14, 2002, which claims the benefit of priority based on German Patent Application 101 14 561.6, filed Mar. 24, 2001 in Germany.

BACKGROUND OF THE INVENTION

1. Field of the Invention

The present invention relates to an agent containing creatine, creatinine and/or their derivatives for the purpose of hardening, improving the luster of, fortifying and improving the structure (restructuring) or increasing the volume of keratinic fibers, particularly damaged keratinic fibers such as damaged human hair.

2. Description of the Related Art

The damaging of keratinic fibers by environmental factors (for example energy-rich radiation), the physiological status (for example age or health of the individual involved) or mechanical and chemical effects is known. The consequences are unfavorable mechanical properties of the affected materials. Such damage of the internal structure of keratinic fibers manifests itself by the loss of hardness, luster, strength, breaking resistance, tensile strength or fiber bundle tensile strength.

Keratinic fibers, particularly human hair, show such effects, in particular, through a lack of luster, reduced tensile strength and poor combability. Said effects are brought about by ageing processes, primarily physiologically related ones or induced by physical (weathering), mechanical (combing, brushing) and chemical factors. Long hair shows these effects especially at the hair tips. Chemical factors consist primarily of bleaching, oxidative dyeing and permanent waving of hair, in which aggressive oxidants and reducing agents are used, preferably in a strongly alkaline medium where they exert their full action. However, other chemical factors, for example water containing high amounts of chlorine or salts, also exert damaging effects on keratin-containing material.

Commercial rinses and treatments contain as active substances mainly cationic surfactants or polymers, waxes and/or oils. The more damaged the hair, the more anionic groups are present at the surface. Cationic compounds are electrostatically attracted to such an oppositely charged surface, whereas oils and waxes interact with the hydrophobic groups of keratin. A structural improvement inside the hair therefore cannot be achieved with such hair-care products.

The use of certain unsaturated compounds, particularly ascorbic acid, in hair-treatment agents for this purpose is known from our own WO 00/57839. In aqueous solution, however, ascorbic acid is not stable for a long time so that such agents cannot be stored, but must be prepared only shortly before use.

The use of creatin and creatin derivatives as moisturizers for cosmetic preparations is known from DE-A 198 41 385. Such preparations are said to improve the elastic properties of the skin and to contribute to the smoothing of wrinkles and to the removal of cracks and dandruff.

SUMMARY OF THE INVENTION

The objective underlying the present invention consists of providing an agent, particularly a cosmetic hair-treatment agent to be used for improving the condition of hair, and which would eliminate the aforesaid drawbacks.

According to the invention, this objective is reached by use of an agent containing creatine, creatinine and/or their derivatives and/or their salts to harden, fortify, restructure, repair or stabilize keratinic fibers or to increase the luster, volume or combability of keratinic fibers.

Surprisingly, we have now found that by use of creatine, creatinine and/or their derivatives and/or their salts the structure of keratinic fibers (hair) is modified so that hardening and fortifying as well as an increase in breaking resistance, tensile strength or bundle tensile strength, particularly in the case of worn and damaged keratinic fibers, take place.

Besides a hair-care effect resulting from the influence on the hair surface (cuticula) to be described in the following, a repairing action, in particular, takes place. This action is attributable to changes within the hair (cortex). Tensile forces were measured which caused oxidatively damaged hair (by bleaching) to break. Surprisingly, we found that hair which after oxidative damage had been treated with an agent containing creatine, creatinine and/or their derivatives and/or their salts showed a significant increase in the forces needed to cause rupture.

This is surprising, because on the basis of the structure of creatine and its derivatives neither their penetration into the hair nor any influence on the protein structures could be anticipated. Moreover, it is known that undamaged, wet hair requires appreciably lower breaking forces (600-900 mN) than dry hair (1000-1500 mN). In view of this, it was to be expected that a moisturizer such as creatine or creatinine would reduce the breaking forces rather than, as was found, increase them.

As a result, not only is a restructuring (repair) of damaged keratinic fibers made possible, but also a protective effect which opposes the damaging of these materials before or during exposure to certain noxae thus preventing or reducing the damage.

Besides these deleterious changes induced by exogenous noxae, the use according to the invention can exert advantageous effects also in conditions or structural changes of keratinic fibers brought about by physiological processes, for example in cases of age-induced brittle hair or fine hair which may be congenital or age-related (baby hair, old-age hair).

Moreover, in this respect we also found that in the case of keratinic fibers, particularly hair, it is possible to achieve, by the use according to the invention, an increase in volume which can have an advantageous effect on hair styling (increase in hair fullness). It is suspected that the effect of the volume increase is in causal relationship with the hair-hardening, hair-strengthening or hair-restructuring action of the agent used according to the invention. This was surprising, because substances that exert a moisturizing effect usually reduce the hair volume.

The object of the invention is therefore the use according to claim 1.

The particularly preferred substances, creatine (M-amidinosarcosine) (formula I) and its cyclization product creatinine (2-imino-1-methylimidazolidin-4-one (formula II) are physiological constituents of human and animal tissues.

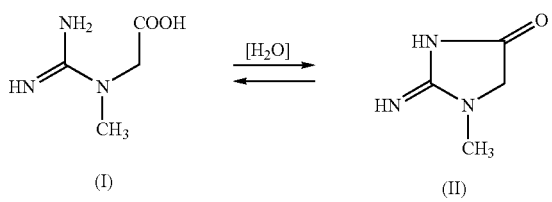

Other particularly preferred substances are creatine phosphate, cyclocreatine, phosphocyclocreatine, guanidine acetate, 3-guanidinepropionic acid, guanidine ascorbate and creatine pyruvate.

According to the invention, creatine, creatinine and/or their derivatives of formulas (III), (IV) or (V) are preferably used

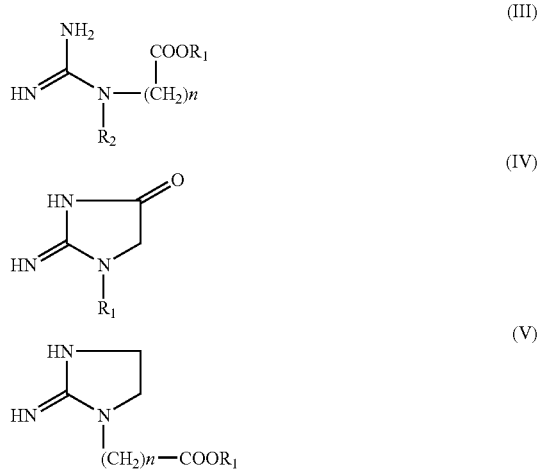

wherein $R_1$ and $R_2$ independently of each other denote H, —$CH_3$, —$CH_2CH_3$ or straight-chain or branched $C_3$- to $C_{22}$-alkyl and n=1 or 2. Preferably, $R_1$ and $R_2$ independently of each other denote H, —$CH_3$, —$CH_2CH_3$ or straight-chain or branched $C_3$- to $C_8$-alkyl and particularly H, —$CH_3$, —$CH_2CH_3$ or —$CH_2CH_2CH_3$.

Any mixtures of creatine, creatinine and/or their derivatives and/or their salts can be used for the said purpose.

Other embodiments of the present invention are indicated in the claims.

For use, the keratinic fibers are brought in contact with an agent containing creatine, creatinine and/or their derivatives and/or their salts, the agent after application preferably being left in place or after an appropriate exposure time being washed out or rinsed off with an aqueous agent.

Preferably, creatine, creatinine and/or their derivatives and/or their salts are contained in the agent in an amount from 0.001 to 30.0 wt. %, preferably from 0.01 to 10.0 wt. % and particularly from 0.05 to 1.0 wt. %, always based on the total amount of the agent.

The agent described for the use according to the invention can be in all appropriate formulations known in the cosmetic or pharmaceutical industries. In particular, the agent can be in the form of an aqueous or aqueous-alcoholic solution, a gel, a cream, an emulsion or a foam, it being possible to package the agent in the form of a one-component preparation as well as in the form of a multicomponent preparation. In the event of a one-component preparation, the agent contains creatine, creatinine and/or at least one of their derivatives and/or salts together with appropriate auxiliary agents or carriers (for example, thickeners, acids, odorants, solvents, salts, wetting agents and/or UV absorbers).

In the event that the agent is in the form of a multicomponent preparation, said agent can consist of at least two different components which are kept spatially separated until they are used. The first component can contain either only the creatine, creatinine and/or at least one of their derivatives and/or salts (active ingredient) underlying the present invention or the active ingredient can be present in said first component mixed with an auxiliary agent (for example a thickener), advantageously in solid, dry form (for example as a powder in compressed or noncompressed form, as a granulate or as a tablet). A second or other component contains only auxiliary agents and carriers.

It is also possible that in a multicomponent preparation different components contain different active ingredients according to the present invention individually or in admixture, either alone or together with different auxiliary agents, the other components containing only auxiliary agents and carriers.

According to the invention, what is covered is the use of a composition characterized in that it is a one-component or multicomponent preparation. If the agent used is a multicomponent preparation, it comprises a first component containing the creatine, creatinine and/or their derivatives and/or their salts with or without auxiliary agents and additives, and a second component which contains the other constituents. Moreover, the agent used as a multicomponent preparation can have at least three different components with at least one of the components containing the creatine, creatinine and/or their derivatives and/or their salts and the other components containing the remaining constituents.

It will be understood that to prepare a ready-to-use agent, the spatially separated individual components of a multicomponent preparation must be mixed shortly before their use according to the invention.

The agent used according to the invention can additionally contain carriers, auxiliary agents, for example solvents such as water, lower aliphatic alcohols, for example ethanol, n-propanol and isopropanol, glycol ethers or glycols such as glycerol and particularly 1,2-propanediol; moreover solubilizers, wetting agents or emulsifiers from the classes of anionic, cationic, amphoteric or nonionic surface-active substances such as the fatty alcohol sulfates, ethoxylated fatty alcohol sulfates, alkyl sulfonates, alkylbenzenesulfonates, alkyltrimethylammonium salts, alkylbetaines, ethoxylated fatty alcohols, ethoxylated nonylphenols, fatty alkanolamides, ethoxylated fatty esters, furthermore thickeners such as the higher fatty alcohols, starch or cellulose derivatives; salts such as, for example, NaCl; buffering agents such as ammonium hydrogen carbonate; thiols, ketocarboxylic acids (oxocarboxylic acids), particularly α-ketocarboxylic acids or their physiologically tolerated salts, UV absorbers, perfumes, dyes, conditioners, hair-swelling agents, preservatives, vaseline, paraffin oil and fatty acids as well as hair-care agents such as cationic resins, lanolin derivatives, cholesterol, pantothenic acid and betaine and propellants such as, for example, propane, butane, dimethyl ether, $N_2$ and carbon dioxide.

The constituents mentioned in the foregoing are used in quantities usually employed for such purposes, for example water in an amount from 0.1 to 95 wt. %, the wetting agents and emulsifiers at a total concentration of 0.2 to 30 wt. %, the alcohols in a total amount from 0.1 to 50 wt. %, the opacifiers, perfume oils, preservatives and dyes in an amount from 0.01 to 5 wt. % each, the buffering agents in a total amount of 0.1 to 10 wt. %, the solubilizers, stabilizers, hair-conditioning and hair-care constituents in an amount from 0.1 to 5 wt. % each, whereas the thickeners and constituents in an amount from 0.1 to 5 wt. % each, whereas the thickeners and solubilizers can be present in said agent in a total amount of 0.5 to 20 wt. %.

The pH of the agent is preferably between 2.0 and 10.0 and particularly between 3.0 to 9.0. If necessary, the desired pH can be achieved by addition of an acid, for example an α-hydroxycarboxylic acid such as lactic acid, tartaric acid, citric acid or malic acid, phosphoric acid, acetic acid, glycolic acid, salicylic acid, glutathione or gluconolactone, or of an alkalinizing agent such as ammonia, an alkanolamine, alkylamine, alkali metal hydroxide, ammonium hydroxide, alkali metal carbonate, ammonium carbonate or alkali metal phosphate.

In the treatment of keratinic fibers, the agent can be left in place (for example on the hair) or it can be rinsed out after use. In the latter case, the agents is allowed to act for 1 to 60 minutes and particularly from 5 to 20 minutes, depending on the temperature (about 20° to 60° C. and preferably 30° to 50° C.), the heat supplied possibly accelerating the restructuring and possibly the increase in volume associated with it). Hence, the application of heat is preferred. At the end of the exposure time, the hair can be rinsed with water and optionally washed with a shampoo.

The formulations suitable for use according to the invention are preferably shampoos, rinses, treatments, foams, fortifiers, hair gels, hair dyes, hair sprays, hair tints, permanent wave agents, fixatives, hair smoothing agents or brillantines.

The agent can also be used as a pretreatment agent before chemical and/or physical treatments of keratinic fibers, particularly before hair dyeing, hair tinting, hair bleaching or permanent hair shaping, for the purpose of preventing hair damage by these oxidative treatments.

We were able to establish that the use according to the invention of an agent containing creatine, creatinine, and/or their derivatives and/or their salts of the present invention brings about an appreciable improvement in the structure of previously damaged keratinic fibers which can be demonstrated on the basis of a statistically highly significant increase in breaking force.

Measurement of the Repair Effect

To determine the breaking force for hair, which is an indicator of the structural integrity of the hair cortex and is thus a measure of the degree of damage, common tensile elongation measurements were performed. From each hair strand, 20 individual hairs were selected and the individual hair diameters were measured with a computer-controlled laser micrometer. The force required to break the individual hairs was then determined with a tensile elongation tester (MTT 160/160 Series Miniature Tensile Tester, serial No. 600.95.05.001, DIA-STRON Ltd, England).

From these individual test results, which because of the differing hair diameters are different, the strand tensile strength (STS) was determined by calculating from the individual values the tensile strength for a hair diameter of 0.08 mm (mean diameter) taking into account the hair diameters. By taking into account the hair density, a conversion to the unit for strand tensile strength (cN/tex) was finally made. The higher the numerical value of the strand tensile strength, the lower is the hair damage.

Measurements made on hair treated with keratin-containing and keratin-free shampoos gave the following results.

Damaged (bleached) hair was treated with the shampoo of Example 2 but without creatine (the creatine was replaced with the same amount of water):

STS=14.8±0.4 cN/tex (determined on 17 hairs from a shampoo-treated strand).

Damaged (bleached) hair treated with the shampoo of Example 2 containing 1 wt. % of creatine:

STS=15.5±0.4 cN/tex (determined on 19 hairs from a shampoo-treated strand).

The difference between the above-indicated mean values is statistically highly significant (significance level determined by the t-test: 99.9%).

The 1 wt. % creatine content increased the strand tensile strength from 14.8 cN/tex to 15.5 cN/tex. This corresponds to an increase of 4.7%. The addition of creatine thus brought about an appreciable hair fortification or repair effect.

Measurement of the Improvement in Combability

The combability of hair is also an important parameter for describing hair quality. Various external influences such as certain cosmetic treatments (bleaching, dyeing permanent waving), weathering and frequent combing and brushing cause a deterioration in hair combability which is attributable to damage to the cuticula.

The principle of most methods for measuring combability consists of measuring the force (combing force) required to move a comb through a hair strand under exactly defined boundary conditions.

Within the framework of our own study, an automated apparatus was used for this purpose. The apparatus had a mechanical grip arm which brought the strands to be studied from a storage location and hung them on a hook of a force-measuring device. The strands were then repeatedly and automatically combed one after another at a constant rate of speed, and for each combing the combing force N (newton) was recorded as a function of the combing path (strand length). The reported combing force values were finally obtained by averaging the combing forces over the combing path. The lower the combing force, the better is the combability of the hair.

Measurements on hair treated with creatine-containing and creatine-free shampoos gave the following results.

Damaged (bleached) hair was treated with the shampoo of Example 2 but without creatine (the creatine was replaced with the same amount of water): The combing force was 1.43±0.05 N (measured average of 3 hair strands treated with shampoo).

Damaged (bleached) hair treated with the shampoo of Example 2 containing 1 wt. % of creatine: The combing force was 1.21±0.08 N (measured average of 3 hair strands treated with shampoo).

The difference between the above-indicated average values is statistically significant (significance level determined by the t-test: 97.5%).

The combing force was reduced by a 1 wt. % creatine content from 1.43 N to 1.21 N, or by 15.3%. In other words, the addition of creatine brought about an appreciable, ascertainable improvement in wet combability of the hair.

Unless otherwise indicated, all percentages in the preceding description are by weight, based on the total weight of the composition involved.

The following examples will more closely explain the subject matter.

EXAMPLES

Example 1

| Hair Spray | |
| --- | --- |
| Vinyl acetate/crotonic acid copolymer | 2.00 wt. % |
| 2-Amino-2-methyl-1-propanol | 0.16 wt. % |
| Ethanol | 37.84 wt. % |
| Creatine | 0.50 wt. % |
| Perfume oil | 0.10 wt. % |
| Propane/butane | to 100.00 wt. % |

Example 2

| Hair Shampoo | |
| --- | --- |
| Sodium lauryl ether sulfate (25% aqueous solution) | 40.0 wt. % |
| NaCl | 4.0 wt. % |
| Creatine | 1.0 wt. % |
| Water | to 100.0 wt. % |

Example 3

| Hair Shampoo | |
| --- | --- |
| Sodium lauryl ether sulfate (25% aqueous solution) | 35.0 wt. % |
| NaCl | 3.0 wt. % |
| Triethanolamine | 4.0 wt. % |
| 1,2-Dibromo-2,4-dicyanobutamine-2-phenoxyethanol | 0.1 wt. % |
| Perfume oil | 0.1 wt. % |
| Creatine | 2.0 wt. % |
| Water | to 100.0 wt. % |

Example 4

| Hair Treatment | |
| --- | --- |
| Glycerol monostearate | 6.0 wt. % |
| Lanolin alkoxylate | 2.0 wt. % |
| Cetyl alcohol | 2.0 wt. % |
| Mixture of lanolin alcohol and paraffin oil | 1.0 wt. % |
| Tris(oligooxyethyl)alkylammonium phosphate | 1.5 wt. % |
| Hydroxyethylcellulose | 20.0 wt. % |
| Citric acid | 0.1 wt. % |
| Sorbic acid | 0.1 wt. % |
| Perfume oil | 0.1 wt. % |
| Creatine | 0.5 wt. % |
| Water | to 100.0 wt. % |

Example 5

| Foam Conditioner | |
| --- | --- |
| PVP/vinylimidazolium methochloride copolymer | 5.00 wt. % |
| PVP/PVA copolymer | 1.00 wt. % |
| Polyoxyethylene-12-cetylstearyl alcohol | 0.15 wt. % |
| Perfume oil | 0.10 wt. % |
| Creatine | 1.00 wt. % |
| Propane/butane | 10.00 wt. % |
| Water | to 100.00 wt. % |

Example 6

| Brillantine | |
| --- | --- |
| Candelilla wax | 80.0 wt. % |
| Paraffin oil | 14.8 wt. % |
| Isopropyl myristate | 4.6 wt. % |
| Perfume oil | 0.5 wt. % |
| Creatine | 0.1 wt. % |
| | 100.0 wt. % |

Example 7

| Permanent Wave Agent | |
| --- | --- |
| Thioglycolic acid (80% aqueous solution) | 9.5 wt. % |
| Ammonia (25% aqueous solution) | 1.6 wt. % |
| Ammonium carbonate | 4.5 wt. % |
| Creatine | 2.0 wt. % |
| Perfume oil | 0.2 wt. % |
| Water | to 100.0 wt. % |

Example 8

| Permanent Wave Fixative | |
| --- | --- |
| Hydrogen peroxide | 4.6 wt. % |
| Citric acid | 0.2 wt. % |
| Creatine | 3.0 wt. % |
| Perfume oil | 0.1 wt. % |
| Water | to 100.0 wt. % |

Example 9

| Oxidative Hair Colorant in Cream Form | |
| --- | --- |
| Stearyl alcohol | 8.00 wt. % |
| Paraffin oil | 13.00 wt. % |
| Wool grease | 6.00 wt. % |
| Perfume | 0.30 wt. % |
| p-Toluylenediamine | 0.70 wt. % |
| Resorcinol | 0.05 wt. % |

-continued

| Oxidative Hair Colorant in Cream Form | |
|---|---|
| Aminophenol | 0.06 wt. % |
| Ethylenediaminetetraacetic acid (EDTA) | 0.20 wt. % |
| Ammonia (25% aqueous solution) | 2.00 wt. % |
| Sodium sulfite | 1.00 wt. % |
| Creatine | 1.00 wt. % |
| Water | to 100.00 wt. % |

The invention claimed is:

1. A method of strengthening or repairing human hair grown out of a scalp of a person, said method consisting of the steps of:
 a) providing a hair treatment composition consisting of
  at least one solvent,
  at least one auxiliary agent,
  at least one pH adjusting agent, and
  at least one active ingredient for strengthening or repairing the human hair grown out of the scalp of the person, wherein said at least one active ingredient is selected from the group consisting of creatine, creatinine, and salts of said creatinine;
  wherein said at least one solvent is selected from the group consisting of water, ethanol, n-propanol, isopropanol, glycols and glycol ethers;
  wherein said at least one auxiliary agent is selected from the group consisting of sodium lauryl ether sulfate, fatty alcohol sulfates, ethoxylated fatty alcohol sulfates, alkyl sulfonates, alkylbenzene sulfonates, alkyltrimethylammonium salts, ethoxylated fatty alcohols, ethoxylated nonylphenols, fatty alkanol amides, ethoxylated fatty esters, fatty alcohols, isopropyl myristate, starch, hydroxyethylcellulose, polyvinylpyrrolidone/vinyl acetate copolymer, polyvinyl pyrrolidone/vinylimidazolium methochloride copolymer, 1,2-dibromo-2,4-dicyanobutamine-2-phenoxylethanol, perfume oils, ammonium hydrogen carbonate, NaCl, p-toluylenediamine, resorcinol, aminophenol, ethylenediaminetetracetic acid, hydrogen peroxide, thioglycolic acid, propane, butane, dimethyl ether, nitrogen, carbon dioxide, paraffin oil, petrolatum, lanolin, lanolin alcohol, lanolin alkoxylate, cholesterol and thiols; and
  wherein said pH adjusting agents are selected from the group consisting of phosphoric acid, acetic acid, glutathione, ammonia, alkanolamines, alkylamines, alkali metal hydroxides, ammonium hydroxide, alkali metal carbonates, ammonium carbonate and alkali metal phosphates;
 b) bringing said hair treatment composition into contact with said human hair;
 c) allowing said hair treatment composition to remain in contact with said human hair for a predetermined exposure time interval; and
 d) rinsing said hair treatment composition from the human hair when said exposure time interval ends;
  wherein said predetermined exposure time interval is from 1 to 60 minutes and said hair treatment composition is at a temperature of between 20° C. and 60° C. during the time interval, or said predetermined exposure time interval is from 5 to 20 minutes and said hair treatment composition is at a temperature of between 30° C. and 50° C. during the time interval.

2. The method as defined in claim 1, wherein said hair treatment composition comprises said water, said pH adjusting agent, from 0.01 to 10.0 percent by weight of said creatine, and said hair treatment composition has a pH of from 3.0 to 9.0.

3. The method as defined in claim 1, wherein said hair treatment composition contains from 0.1 to 3.0 wt. % of said creatine, based on a total amount of said hair treatment composition.

4. A method of increasing volume or combability of human hair grown out of a scalp of a person, said method consisting of the steps of:
 a) providing a hair treatment composition consisting of
  at least one solvent,
  at least one auxiliary agent,
  at least one pH adjusting agent, and
  at least one active ingredient for increasing volume or combability of the human hair grown out of the scalp of the person, wherein said at least one active ingredient is selected from the group consisting of creatine, creatinine, and salts of said creatinine;
  wherein said at least one solvent is selected from the group consisting of water, ethanol, n-propanol, isopropanol, glycols and glycol ethers;
  wherein said at least one auxiliary agent is selected from the group consisting of sodium lauryl ether sulfate, fatty alcohol sulfates, ethoxylated fatty alcohol sulfates, alkyl sulfonates, alkylbenzene sulfonates, alkyltrimethylammonium salts, ethoxylated fatty alcohols, ethoxylated nonylphenols, fatty alkanol amides, ethoxylated fatty esters, fatty alcohols, isopropyl myristate, starch, hydroxyethylcellulose, polyvinylpyrrolidone/vinyl acetate copolymer, polyvinyl pyrrolidone/vinylimidazolium methochloride copolymer, 1,2-dibromo-2,4-dicyanobutamine-2-phenoxylethanol, perfume oils, ammonium hydrogen carbonate, NaCl, p-toluylenediamine, resorcinol, aminophenol, ethylenediaminetetracetic acid, hydrogen peroxide, thioglycolic acid, propane, butane, dimethyl ether, nitrogen, carbon dioxide, paraffin oil, petrolatum, lanolin, lanolin alcohol, lanolin alkoxylate, cholesterol and thiols; and
  wherein said pH adjusting agents are selected from the group consisting of phosphoric acid, acetic acid, glutathione, ammonia, alkanolamines, alkylamines, alkali metal hydroxides, ammonium hydroxide, alkali metal carbonates, ammonium carbonate and alkali metal phosphates;
 b) bringing said hair treatment composition into contact with said human hair;
 c) allowing said hair treatment composition to remain in contact with said human hair for a predetermined exposure time interval; and
 d) rinsing said hair treatment composition from the human hair when said exposure time interval ends;
  wherein said predetermined exposure time interval is from 1 to 60 minutes and said hair treatment composition is at a temperature of between 20° C. and 60° C. during the time interval, or said predetermined exposure time interval is from 5 to 20 minutes and said hair treatment composition is at a temperature of between 30° C. and 50° C. during the time interval.

5. The method as defined in claim 4, wherein said hair treatment composition comprises said water, said pH adjusting agent, from 0.01 to 10.0 percent by weight of said creatine, and said hair treatment composition has a pH of from 3.0 to 9.0.

6. The method as defined in claim 4, wherein said hair treatment composition contains from 0.1 to 3.0 wt. % of said creatine, based on a total amount of said hair treatment composition.

* * * * *